United States Patent [19]
Delvigo

[11] Patent Number: 5,925,028
[45] Date of Patent: Jul. 20, 1999

[54] BLOOD OR HEMO-DERIVATIVES TRANSFUSION DEVICE

[75] Inventor: Pierluigi Delvigo, Camogli, Italy

[73] Assignee: Diesse di Soster Carmen & C. S.n.C., Camogli, Italy

[21] Appl. No.: 08/746,308

[22] Filed: Nov. 8, 1996

[30] Foreign Application Priority Data

Nov. 16, 1995 [IT] Italy .................................. GE95A0125

[51] Int. Cl.$^6$ .................................................. A61B 19/00
[52] U.S. Cl. ........................... 604/404; 604/403; 604/410
[58] Field of Search .................................... 604/403–416, 604/80

[56] References Cited

U.S. PATENT DOCUMENTS

| | | | |
|---|---|---|---|
| 3,853,126 | 12/1974 | Schulte | 128/214 |
| 4,150,673 | 4/1979 | Watt | 128/272 |
| 4,219,021 | 8/1980 | Fink | 128/214 |
| 4,280,723 | 7/1981 | Moldestad | 285/376 |
| 4,496,349 | 1/1985 | Cosentino | 604/175 |
| 4,619,640 | 10/1986 | Potolsky et al. | |
| 5,423,750 | 6/1995 | Spiller | 604/80 |

FOREIGN PATENT DOCUMENTS 2 593 706  7/1987  France .
2 063 684  10/1981  United Kingdom .

*Primary Examiner*—John G. Weiss
*Assistant Examiner*—Ki Yong O
*Attorney, Agent, or Firm*—Larson & Taylor

[57] ABSTRACT

Device for the transfusion of blood or hemo-derivatives including: a blood or hemo-derivatives container; a device for the transfusion of blood or hemoderivatives to the patient; and a device for connecting the container to the device for the transfusion; the device for connecting includes a joint formed by two central tubular mutually connectable members, both provided with complementary coding devices, and device for locking the connectable members together.

11 Claims, 6 Drawing Sheets

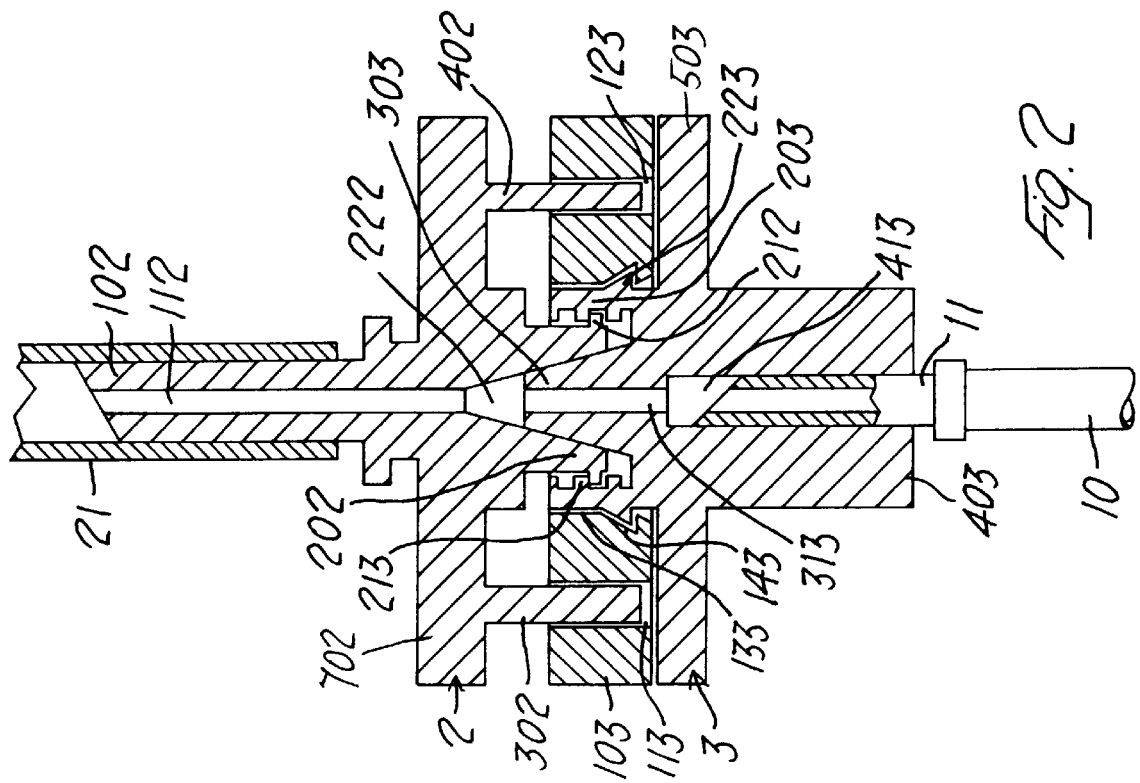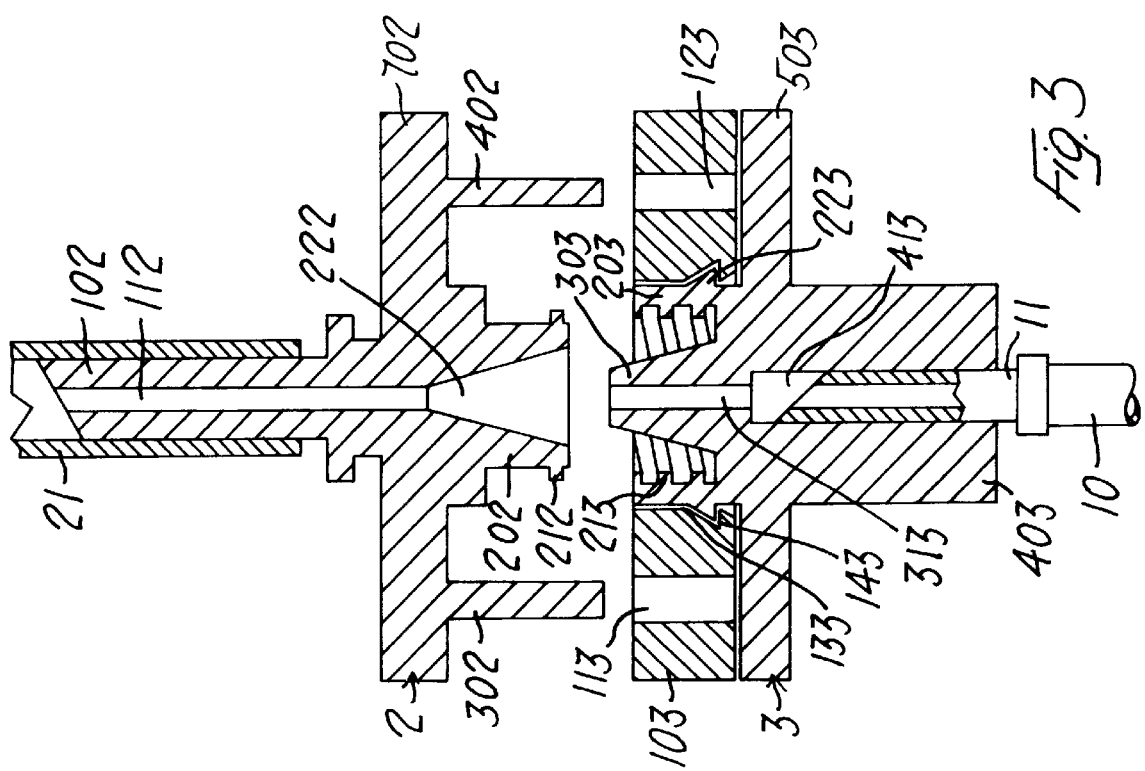

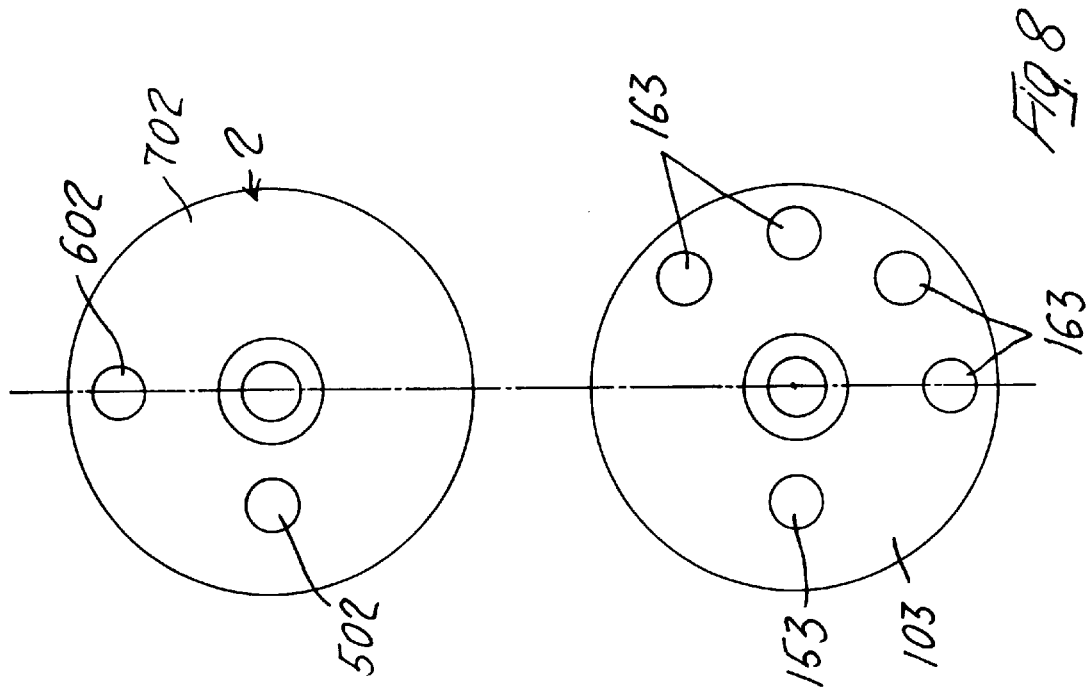
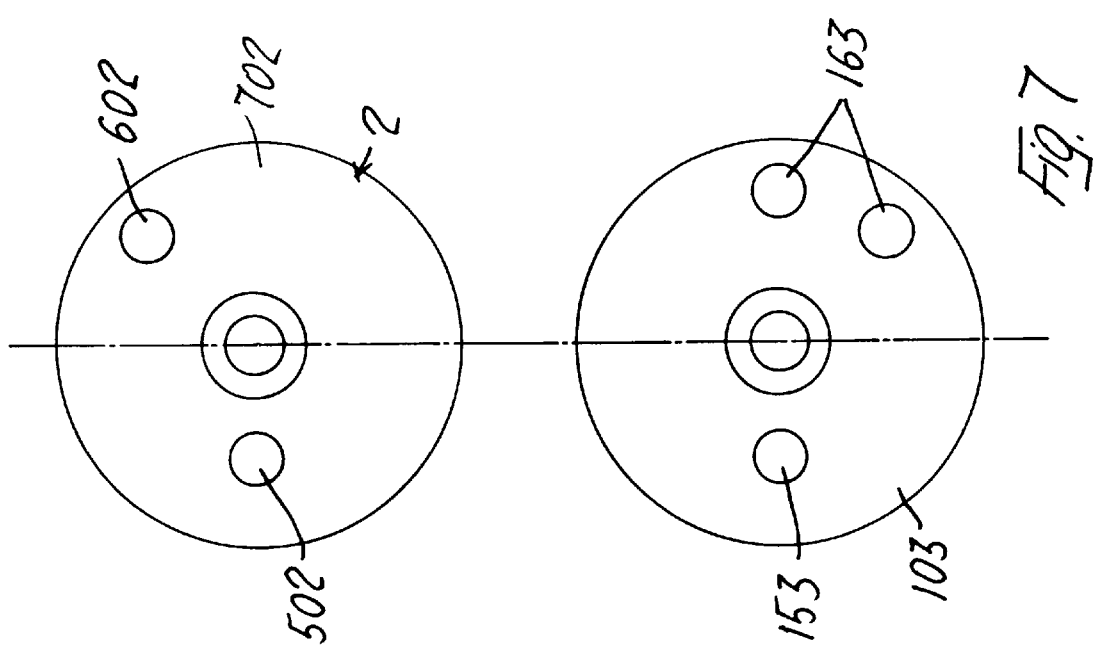

BLOOD OR HEMO-DERIVATIVES TRANSFUSION DEVICE

BACKGROUND OF THE INVENTION

The present invention relates to a device for the transfusion of blood or hemo-derivatives products.

Usually, transfusions are carried out by connecting the means of transfusion of fluid to the patient, such as for instance a defluxor connected to a venous catheter, to a blood or hemo-derivatives container. A serious problem, arising practically at each transfusion to be carried out, is that the patient to be transfused be receiving a blood or hemo-derivative which is compatible with the group of the blood of patient. The above control on the group of the blood or hemo-derivative directed to the patient is usually carried out at a visual level, and can be affected by mistakes or slips, especially in emergency conditions.

SUMMARY OF THE INVENTION

A task of the present invention is to introduce in a transfusion device a control system preventing in a sure and positive manner any connection between the container and the transfusion means whenever the blood or hemo-derivative in the container is not compatible with the blood of the patient.

An object of the present invention is therefore a device for the transfusion of blood or hemo-derivatives comprising: a blood or hemo-derivatives container; means for the transfusion of blood or hemoderivatives to the patient; and means for connecting said container to said means for transfusion, characterized in that said connecting means comprise a joint formed by two central tubular mutually connectable members, both provided with complementary coding means and with means for locking said connectable members together.

According to one preferred embodiment of the invention, such coding means comprise at least two pins projecting from one of such members parallelly to the axis of the such joint, the other member being provided with a plate having two or more holes complementary and coaxial to said pins.

BRIEF DESCRIPTION OF THE DRAWINGS

Further advantages and features will become evident from the following description of some preferred embodiments of the present invention shown, by way of non-limiting examples, in the annexed drawings, in which:

FIG. 2 is a longitudinal sectional view through a particular of the device shown in FIG. 1, with the two members of the joint connected together;

FIG. 3 is a view similar to that in FIG. 2, in which the two members of the joint are disconnected;

FIGS. 5 to 8 show diagrammatically the coding system used according to a further embodiment of the present invention.

DESCRIPTION OF THE PREFERRED EMBODIMENTS OF THE INVENTION

Figure 1:
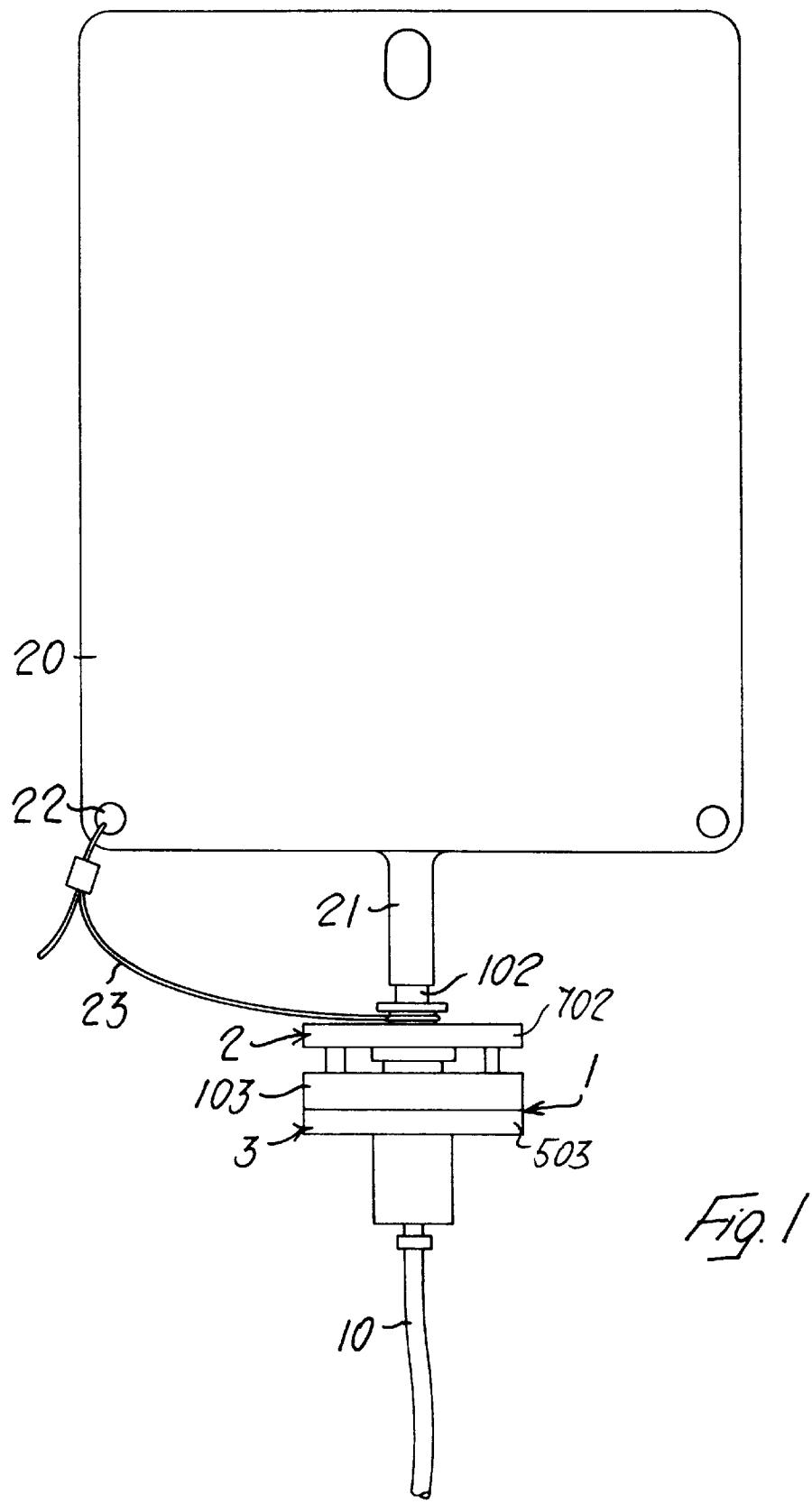
FIG. 1 is a side elevational view of a first embodiment of the transfusion device according to the present invention.

With reference to the drawings, in FIG. 1 is shown the transfusion device according to the invention; with numeral 1 is designated the joint connecting the tube 10 of the means of transfusion to the patient to the blood or hemo-derivatives container, that is, the bag 20. The joint 1 is formed by two members 2 and 3, connected one to another in the way better described later on. The end of the member 2 opposed to that connected with the member 3 shows a tubular element 102 (see FIGS. 2 and 3) that is inserted into the hose 21 of the bag 20. The tubular element 102 of the member 2 is fixed to the bag 20 by means of the strip 23 which is tied to a hole 22 formed on the edge of the bag 20. The member 3 is further provided with a a plate 103 directed toward the member 2, for the purpose which will be later described.

In FIGS. 2 and 3 the joint 1 of the device according to the invention is shown in section. The joint 1 comprises the member 2, consisting of disc-like member 702. Centrally, from one side of the member 702 a tubular element 102 projects upwardly. The element 102 is made integral with the member 702 and is provided with an axial duct 112 extending up to the opposite side of the member 702. The tubular element 102 fits into the hose 21 of the bag 20. On its opposite side, the member 702 is provided with a cylindrical extension 202 provided with an axial tapered recess 222 communicating with the duct 112 and further provided on its outer surface with two teeth 212 projecting radially. Two pins 302 and 402 of different cross section project parallelly to the axis of tubular element 102.

The member 3 also consist of a disc-like member 503, from which projects centrally, on the side facing the member 2, a cylindrical bush 203 inside provided with a thread 213. On the center of said bush 203 is formed a tapered extension 303, which is axially provided with a duct 313. On its opposite side, the member 503 is provided with a cylindrical body 403, axially provided with a recess 413, communicating with the duct 313; in the recess 413 is lodged the end 11 of the tube 10 of the transfusion means. The bush 203 is provided on its lateral outer surface with the annular rib 223, cooperating with the groove 143 formed on the wall of the axial hole 133 of the plate 103. The plate 103 has also the holes 113 and 123 respectively complementary to the pins 302 and 402.

Figures 4A, 4B:
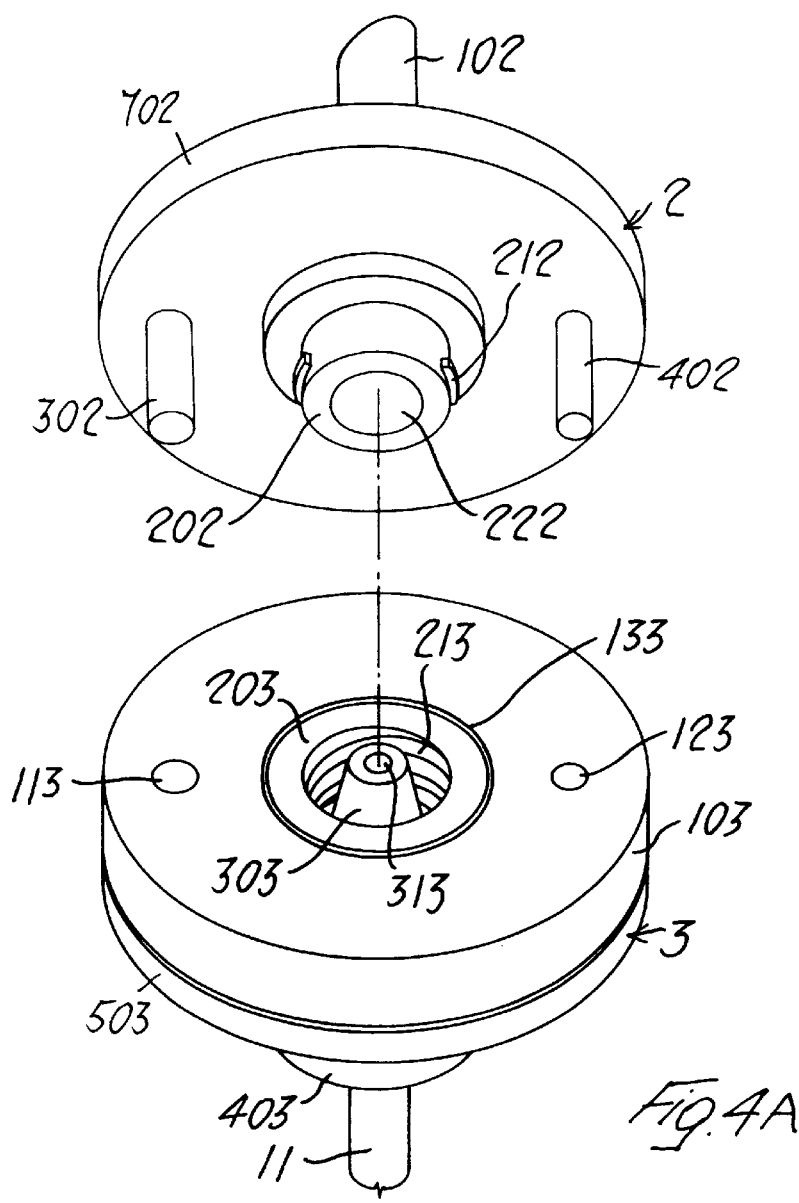
FIG. 4A is a perspective view of the members shown in FIGS. 2 and 3.
FIG. 4B is a control platelet to be used in conjunction with the transfusion device of the invention.

In FIG. 4B, the numeral reference 4 designates a recognition platelet, provided to the patient at the time of the determination of his blood group. Such platelet shows a reproduction of the geometry of holes of the plate 103 of a member 3 of joint 1 that can be used on transfusion means. The platelet 4 is provided with the holes 104 and 204, placed like the holes 113, 123 of the plate 103 of the member 3. This insight provides a further utility to the personnel attending to such operations, further lowering the hazard of mistakes.

Figure 6:
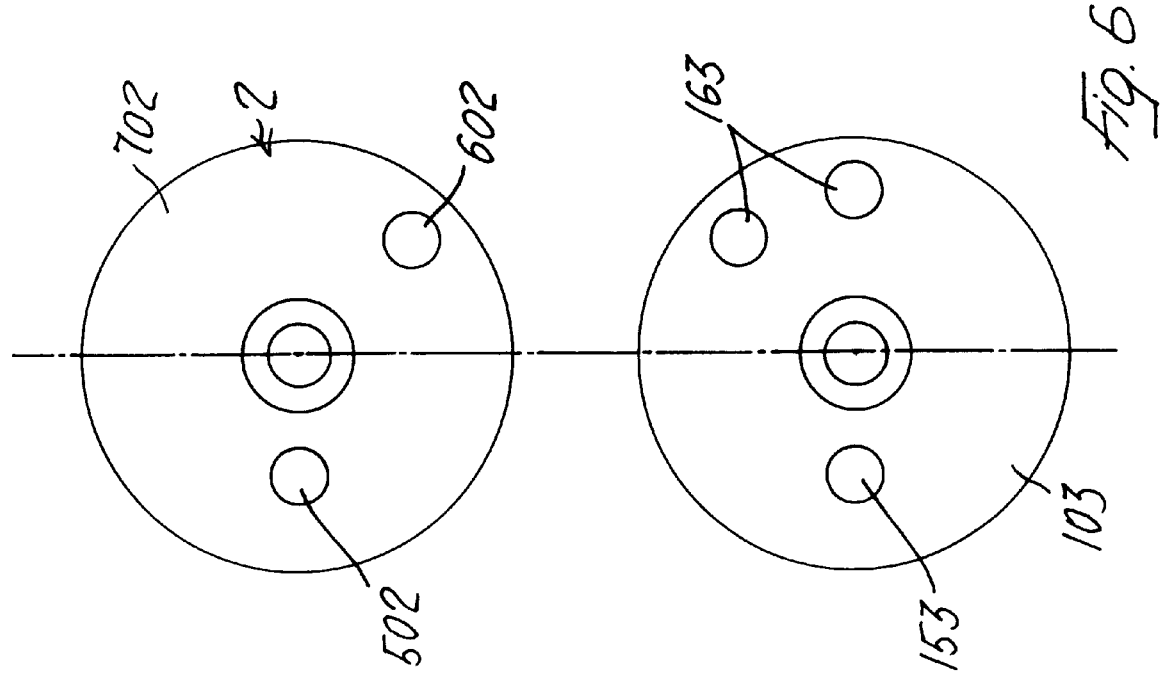
Figure 5:
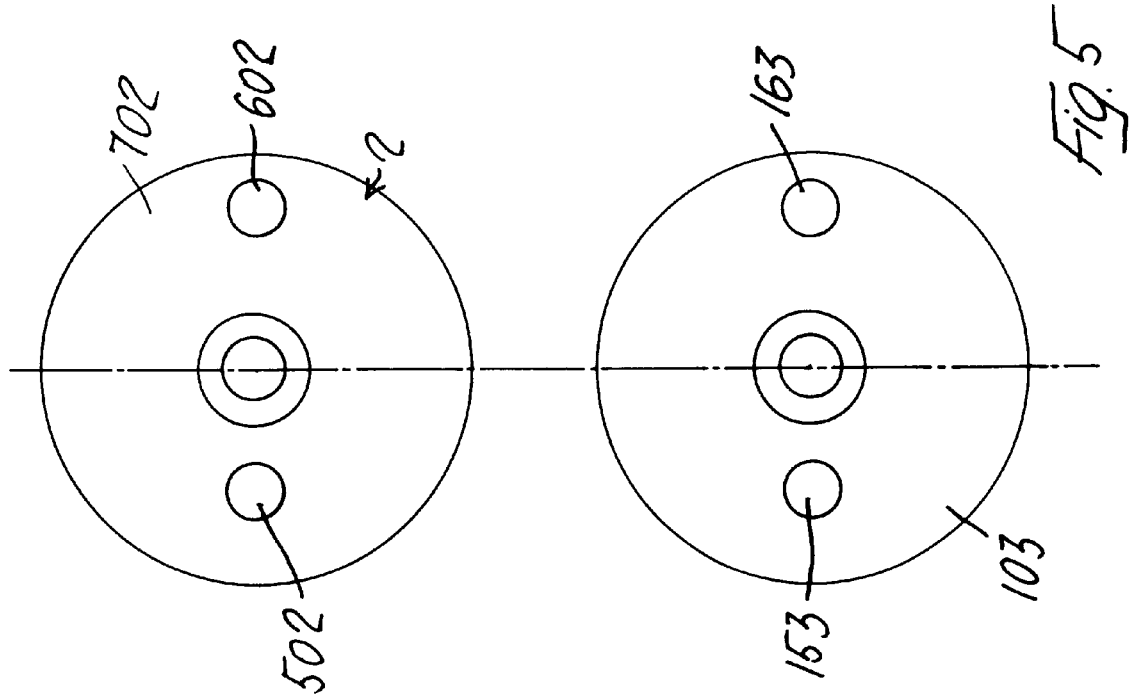

In FIGS. 5 to 8 is diagrammatically shown an embodiment of the coding system used in the transfusion device according to the present invention. In FIG. 5 are shown, side by side, the face of the disc-like member 702 of the member 2 having the pins 502 and 602, which are different from the pins described above in that they have both the same section, and the face of the plate 103 of the member 3, having the holes 153 and 163, which have also the same section. In FIG. 6 is shown the member 2 having the pin 602 in a different position from that of FIG. 5, and the plate 103 has one hole 153 and two holes 163. The situation shown in FIG. 7 is almost the same, except for the pin 602 that is in specular position in respect to that illustrated in FIG. 6, and the holes 163 are likely placed on the plate 103. In FIG. 8, the pin 602 is in another different position, and the plate 103 has four holes 163.

Figure 9:
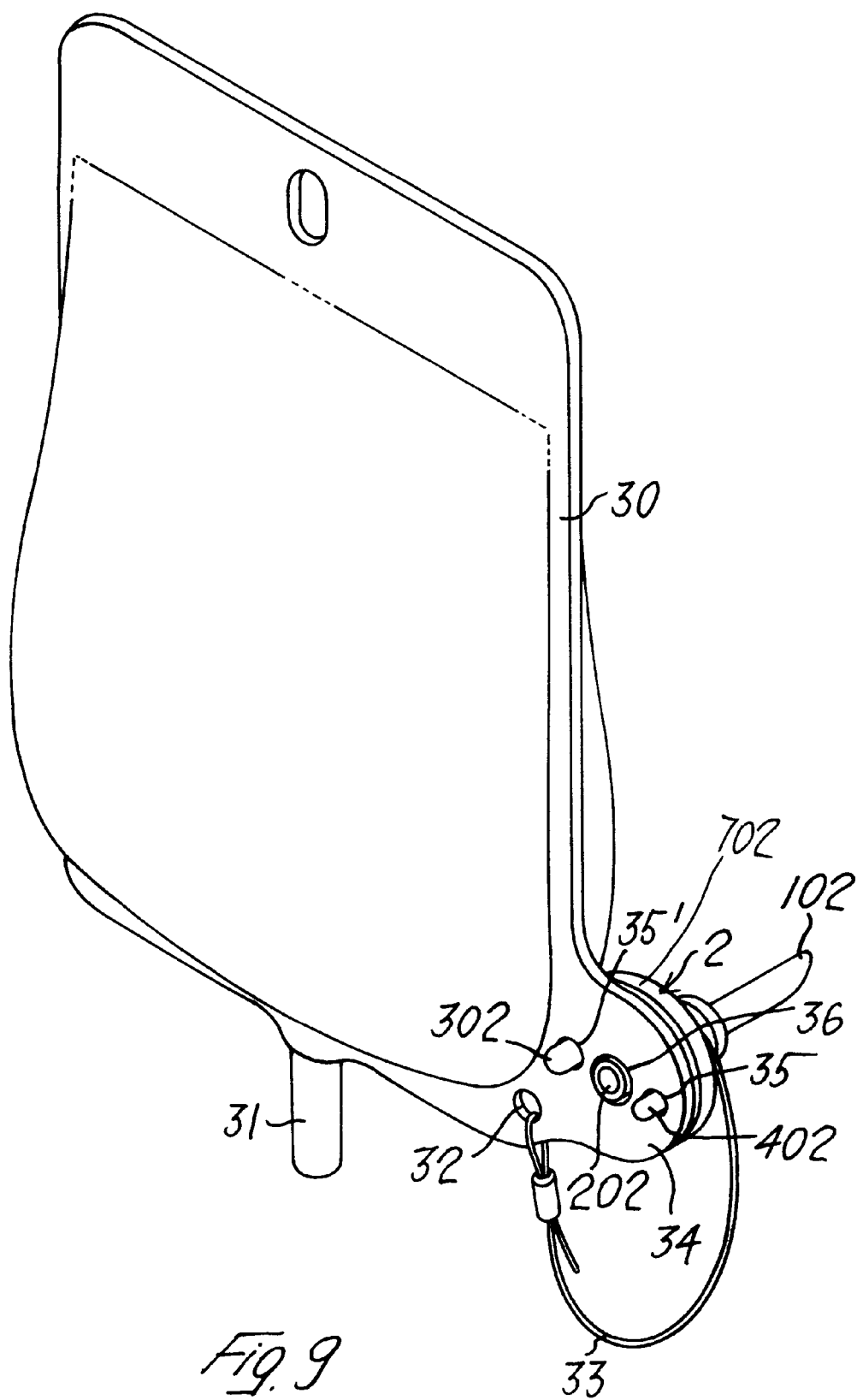
FIG. 9 is still another embodiment of the device according to the invention.

In FIG. 9 is finally shown a further embodiment of the device according to the present invention. The bag 30, similar to the bag 20 shown in FIG. 1, has, at one side, at its end provided with the hose 31, a limb 34 provided with three holes: a central hole 36 and two side holes 35 and 35' diametrically opposed in respect to such central hole 36. The member 2 of the joint 1 of the device of the invention, previously described, is placed with the two pins 302 and 402 lodged into the holes 35 and 35' respectively, and the extension 202 fitted into the hole 36 of the limb 34. The member 2 is further linked with the strip 33 connected at one end to the tubular element 102 of the member 2 and at the other end to the hole 32 formed on the peripheral edge of the bag 30.

The operation of the transfusion device according to the invention will become evident as following. As it is known, normally to the blood or hemo-derivatives containers there is applied, at the manufacturing, an identifying label of the group of the blood or hemo-derivative contained in it. The simple visual identification by the operator can be yet, in certain cases, cause of mistakes. According to the present invention, during the manufacturing step the member 2 of the joint 1 is coupled to the container, the bag 20 in the case shown in FIG. 1, by linking the same to the bag with the strip 23. When the transfusion has to be carried out, the bag is chosen on the grounds of the compatibility of its contents with the blood of the receiving patient. Practically, the member 2 coupled to the bag is compared with the member 3, which has been mounted at an end of the means of transfusion, normally comprising a tube 10 connected to a defluxor in its turn connected to a venous catheter. The member 2 shall have the pins 302, 402 on its disc-like member 702 placed in such way that said pins can correctly match with the holes 113, 123 of the plate 103 of the member 3. The matching being verified, the member 2 and the member 3 of the joint 1 can be steadly connected turning the member 503 in such way as to lock the threaded bush 203 and the extension 202 of the member 702 one to another. The contents of the bag 20 can now flow in the tube 10 and then to the defluxor and finally to the patient.

As shown in FIGS. 5 to 8, by varying the position of the pins on the disc-like member 702 of the member 2 and the position of the holes on the plate 103 of the member 3 of the joint 1, there can be obtained the codings, for example necessary to the selection of the different compatibility of a patient to the blood contained in the bag 20. As it is known, to the different blood groups correspond different compatibilities, in facts, if the pins 502, 602 placed as shown in FIG. 5 represent a group O donor, the group O receiver will have on the plate 103 of the member 3 connected to his means of transfusion, the holes as shown in this Figure. The patient having group A blood will have a member 3 with a plate 103 of the kind shown in FIG. 6, and then this plate will be compatible either to the group O blood or to the group A blood. In the same way it will happen for the group B patient, that there will be provided with the member 3 having the plate 103 shown in FIG. 7. Finally, the group AB patient will be compatible to the blood of the donors of every group, and the plate 103 of its member 3 will be formed appropriately, as shown in FIG. 8.

Advantageously, either in the embodiment shown in FIGS. 1 to 4A, or in the embodiment shown in FIGS. 5 to 8, the two pins placed on the member 2 of the joint 1 are different one to another. In the former case, the two pins lay on the same circumference, but the pin 302 has a bigger cross section than the pin 402; moreover, the position of the pin 402 is variable, whilst that of the pin 302 is fixed. Such an insight has the purpose of preventing the incorrect fitting of the pins 302, 402 in the holes 113, 123 of the plate 103; the holes will be correspondingly of respectively different section. In the latter case shown in FIGS. 5 to 8, the same target is achieved with pins and holes of the same section, but laid on different circumferences. Also in this case, there is only one way to match the members of the joint one to another.

As described for the coupling during the manufacturing step of the member 2 with the bag 20, linking such member to the bag by the strip 23, the embodiment shown in FIG. 9 allows to carry out such a coupling in a more careful and practical way. Thus, the pins being fitted into the holes 35, 35' of the limb 34, the loss or disengagement of the member 2 from the bag can be prevented. Obviously, the holes 35, 35' shall be complementary to the pins 302, 402 of the member 2 linked to the bag. By this way, a control of the contents of the bag 30 is then achieved, each pair of holes 35, 35' identifying a specific content of the bag 30.

The transfusion device according to the invention minimize in the way above described the hazard of mistake in the administration to the patients of blood or hemo-derivatives, then increasing the safety in the transfusion operations, and without excessive complications of the operations.

What I claim is:

1. A system for transfusions of blood products to patients, wherein there are at least first and second types of blood products and wherein there are first types of patients who may only receive the first type of blood product and second types of patients who may receive either the first or second types of blood product, said system comprising:

respective first and second blood product containers associated with the respective first and second types of blood product;

a transfusion means for transfusing of the blood product to the patient; and a connecting means for connecting, via said transfusion means, (i) said first container only to the first type of patient and (ii) said first or second container to the second of patient, said connecting means including a) first and second types of male connectable members and first and second types of female connectable members, selected ones of said male and female connectable members being connected to respective ones of said containers and transfusion means of a same type and for subsequent joining together along a joint axis, said first and second types of male connecting members including respective first and second types of a male coding mechanism, each type of said male coding mechanism including at least two male members with (i) a pattern of said first type of male coding mechanism corresponding to the first type of blood product and (ii) a pattern of said second type of male coding mechanism being different from the pattern of said first type of male coding mechanism and corresponding to the second type of blood product, said first and second types of female connecting members including respective first and second types of a female coding mechanism, (i) said first type of said female coding mechanism including at least two female members with a pattern which mates with the pattern of the first type of said male coding mechanism but not with the second type of said male coding mechanism, and (ii) said second type of said female coding mechanism including at least three female members with a pattern which mates with the patterns of both the first type and second type of male coding mechanisms, whereby (i) first types of patients utilize only first types of male and female connecting members to assure that only first types of blood products are transfused thereto and (ii) second types of patients utilize only second types of male connecting members and either first or second types of female connecting members so that first or second types of blood products are transfused thereto; and b) a locking means for locking mating said male and female connectable members together.

2. A system for transfusions of blood products as claimed in claim 1:

wherein said male members are pins projected parallel to the joint axis; and wherein said female members are holes complementary to said male members.

3. A system for transfusions of blood products as claimed in claim 2:

wherein said male connectable members are connected to said containers and said female connectable members are connected to said transfusion means.

4. A system for transfusions of blood products as claimed in claim 3:

wherein said pins are located equidistant from the joint axis.

5. A system for transfusions of blood products as claimed in claim 3:

wherein there are at least two different diameters of said pins and at least two different diameters of said holes.

6. A system for transfusions of blood products as claimed in claim 3:

wherein said pins all have a same diameter and said holes all have a same diameter complimentary to the diameter of said pins.

7. A system for transfusions of blood products as claimed in claim 3:

wherein there are at least two different radial spacings of said pins and complementary said holes from the joint axis.

8. A system for transfusions of blood products as claimed in claim 3:

wherein said locking means comprises a bush provided on one of said male and female connecting members and an extension cooperating with said bush provided on the other of said male and female connecting members; and wherein said female connecting members are connected to said transfusion means and include a free-rotating plate in which said holes are formed.

9. A system for transfusions of blood products as claimed in claim 3 and further including a linking means separate from said connecting means for linking the selected ones of said male and female connectable members to said containers prior to being connected thereto.

10. A system for transfusions of blood products as claimed in claim 9:

wherein said male connecting members are linked to said containers; and wherein said linking means includes a limb projecting sidewise from said container and holes in said limb provided in a pattern complementary to an associated said pattern of said male coding mechanism of said male connecting member.

11. A system for transfusions of blood products as claimed in claim 1 and further including a recognition element which reproduces the mating patterns of said male and female coding members whereby checking of male and female coding members being used can be made.

* * * * *